(12) United States Patent
Conway

(10) Patent No.: US 6,822,571 B2
(45) Date of Patent: Nov. 23, 2004

(54) PATIENT MOVEMENT DETECTION SYSTEM FOR A BED INCLUDING A LOAD CELL MOUNTING ASSEMBLY

(75) Inventor: Kevin P. Conway, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 36 days.

(21) Appl. No.: 10/253,692

(22) Filed: Sep. 24, 2002

(65) Prior Publication Data

US 2003/0090383 A1 May 15, 2003

Related U.S. Application Data

(60) Provisional application No. 60/334,627, filed on Nov. 15, 2001.

(51) Int. Cl.[7] .............................................. G01G 19/52
(52) U.S. Cl. ................. 340/573.1; 340/665; 340/573.4; 177/144; 5/611; 5/616
(58) Field of Search .......................... 340/573.1, 573.4, 340/665; 177/144; 5/600, 611, 616, 620, 81.1 R, 83.1, 86.1

(56) References Cited

U.S. PATENT DOCUMENTS

| | | | |
|---|---|---|---|
| 3,958,283 A | * 5/1976 | Adams et al. ................. 5/616 |
| 4,025,972 A | * 5/1977 | Adams et al. ................. 5/616 |
| 5,276,432 A |   1/1994 | Travis ...................... 340/573.4 |
| 5,438,723 A | * 8/1995 | Carroll ......................... 5/620 |
| 5,747,745 A | * 5/1998 | Neuman ..................... 177/132 |
| 5,861,582 A | * 1/1999 | Flanagan et al. ........... 177/144 |
| 5,990,423 A | * 11/1999 | Ashpes et al. ............. 177/140 |
| 6,133,837 A | * 10/2000 | Riley ...................... 340/573.1 |
| 6,518,520 B2 | * 2/2003 | Jones et al. ................. 177/144 |
| 6,526,611 B2 | * 3/2003 | Flynn et al. .................. 5/611 |
| 2002/0023785 A1 | * 2/2002 | Sternberg et al. ........... 177/144 |

OTHER PUBLICATIONS

U.S. Published patent application No. 2002/0023785, published Feb. 28, 2002, Inventor: Louis E. Sternberg (8 pgs).

* cited by examiner

Primary Examiner—Jeffery Hofsass
Assistant Examiner—Anne V. Lai
(74) Attorney, Agent, or Firm—Flynn, Thiel, Boutell & Tanis, P.C.

(57) ABSTRACT

A load cell mounting assembly for a bed. The bed includes a base unit. Two pairs of lift arms are pivotally attached to the base unit. Extending between each pair of lift arms is a torque bar. A frame is secured to the torque bars by a plurality of torque bar mounting brackets. Coupled to each torque bar are a number of load cells. The load cells are electrically connected to a control unit that is configured to receive signals from the load cells and to determine patient information from the load cell signals. When the bed is in its lowest position, the load cells engage the floor and the bed is supported only by the load cells.

15 Claims, 5 Drawing Sheets

PATIENT MOVEMENT DETECTION SYSTEM FOR A BED INCLUDING A LOAD CELL MOUNTING ASSEMBLY

This application claims the benefit of Provisional Application No. 60/334,627, filed Nov. 15, 2001.

FIELD OF THE INVENTION

This invention relates generally to a patient movement detection system for a bed and, more particularly, to a load cell mounting assembly that can be retrofitted to an existing bed wherein patient movement can be detected and evaluated while a substantial portion of the patient's weight is still supported on the patient support device.

BACKGROUND OF THE INVENTION

In a healthcare setting, it is often necessary to monitor a patient in order to ensure that the patient remains in bed. For example, a patient who is subject to dizziness upon standing up might fall and injure himself if he leaves the bed without help. Consequently, it is desirable that a caretaker be alerted when such a patient attempts to move from the bed so the patient can be helped.

One early technique for automatically detecting patient exit from a bed was characterized by a normally-closed mechanical switch mechanism positioned between the upper surface of the mattress and the patient or between the lower surface of the mattress and the support frame. The switch was configured so that the weight of the patient was sufficient to open the switch and the absence of the patient's weight allowed the switch to return to its closed position. The switch could be connected in series with a source of power, such as a battery, and with an alarm, such as a buzzer, and would cause the alarm to produce an audible noise when the patient rose from the bed.

Modern patient movement detection systems include a plurality of load cells that support the bed and a detecting arrangement that is responsive to the load cells for detecting movement of the patient from the frame, and thus the bed. The detecting arrangement determines a location of a center of gravity of the patient with respect to the support frame and determines whether the location of the center of gravity is within a predetermined region. One known system of this type is disclosed in U.S. Pat. No. 5,276,432 which issued to Travis on Jan. 4, 1994 (the '432 patent"). While known systems of this type have been adequate for their intended purposes, they have not be satisfactory in all respects.

For instance, the load cells and associated transmitting hardware and software of the Travis patent are built into the frames of the bed support device, thereby preventing utilizing of the patient movement detection system with any existing beds. These integrated systems can be expensive and are often cost prohibitive for many health care facilities, which would be faced with replacing existing beds to take advantage of this detection system. Since load cell based center of gravity patient movement detection systems are more reliable than the early switch methods, it is desirable to develop an affordable load cell based system that can be retrofitted onto an existing bed in any health care facility.

SUMMARY OF THE INVENTION

This invention is directed to a new and useful patient movement detection system that can be retrofitted to an existing bed. The bed includes a base unit. Two pairs of lift arms are pivotally attached to the base unit. Extending between each pair of lift arms is a torque bar. A frame is secured to the torque bars by a plurality of torque bar mounting brackets. Coupled to each torque bar are a number of load cells. The load cells are electrically connected to a control unit that is configured to receive signals from the load cells and to determine patient information from the load cell signals. When the bed is in its lowest position, the load cells engage the floor and the bed is supported only by the load cells.

BRIEF DESCRIPTION OF THE DRAWINGS

This invention is pointed out with particularity in the accompanying claims. The above and further features and benefits of this invention are better understood by reference to the following detailed description, as well as by reference to the following drawings in which:

DETAILED DESCRIPTION

Figure 1:
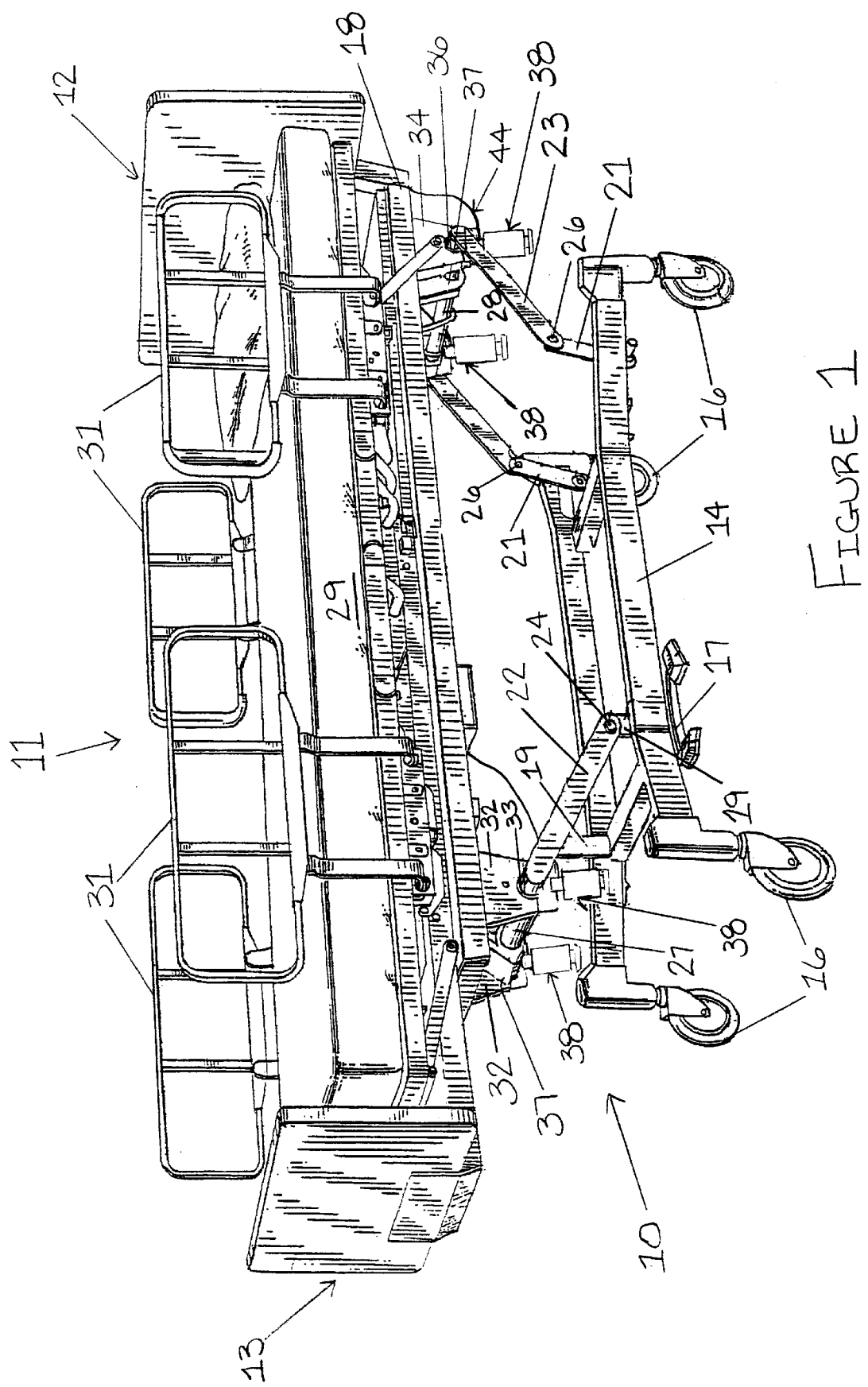
FIG. 1 is an isometric view of a hospital bed according to the present invention.

Referring to FIG. 1, there is illustrated a hospital bed 11 including a patient movement detection system 10 according to this invention. The bed 11 has a head end 12 and a foot end 13 and is supported by a base unit 14. If it is desired to render the bed 11 easily movable, a plurality of wheels 16 can be provided on the base unit 14 at the four corners thereof. A pedal 17 extends from the base unit 14 to facilitate locking and unlocking of the wheels 16.

Four generally upright pivot plates 19 and 21 extend upward from the base unit 14. As illustrated, two pivot plates 21 are rigidly attached to the head end 12 of the base unit 14 and two pivot plates 19 are rigidly attached to the foot end 13. Since the pivot plates 19 and 21 are attached to the base unit 14 in a rigid manner, they cannot move with respect to the base unit 14.

A lift arm 22 is pivotally attached to an upper end of each pivot plate 19 at a pivot point 24. The lift arms 22 can be attached to the respective pivot plate 19 by a bolt or other fastening means that secures the lift arms 22 to the pivot plates 19 while still allowing the lift arms 22 to pivot at the pivot point 24. A torque bar 27 is secured to and extends between the free ends of the lift arms 22. A lift arm 23 is pivotally attached to an upper end of each pivot plate 21 at a pivot point 26. The lift arms 23 can be attached to the pivot plates 21 in a manner similar to that disclosed for attachment of the lift arms 22 to the pivot plates 19. A torque bar 28 is secured to and extends between the free ends of the lift arms 23. The torque bars 27 and 28 are rigidly attached to their respective lift arms 22 and 23. Thus, transverse movement of the torque bars 27 and 28 toward and away from each other will cause the respective lift arms 22 and 23 to rotate together about the associated pivot points 24 and 26.

A frame 18 is supported on the torque bars 27 and 28. The frame 18 supports a mattress 29 or other suitable patient support surface. A plurality of side rails 31 can, if desired, extend upward around the mattress 29, as illustrated.

Extending downward from the head end 12 of the frame 18 are two torque bar brackets 34. Two torque bar brackets 32 extend downward from the foot end 13 of the frame 18. Each torque bar bracket 32, 34 is shaped to fit over the associated torque bar 27, 28. A bushing 33 is secured between each bracket 32 and the torque bar 27. A bushing 36 is secured between each bracket 34 and the torque bar 28. Rotation of the lift arms 22 and 23 causes the respective torque bar 27, 28 to raise or lower with respect to the floor. When the torque bars 27 and 28 move in this manner, they rotate in the associated bracket 32 and 34, while exerting an upward or downward force on the bracket, and therefore on the frame 18. Thus, the bed will be raised or lowered when the lift arms 22 and 23 rotate.

Figure 2:
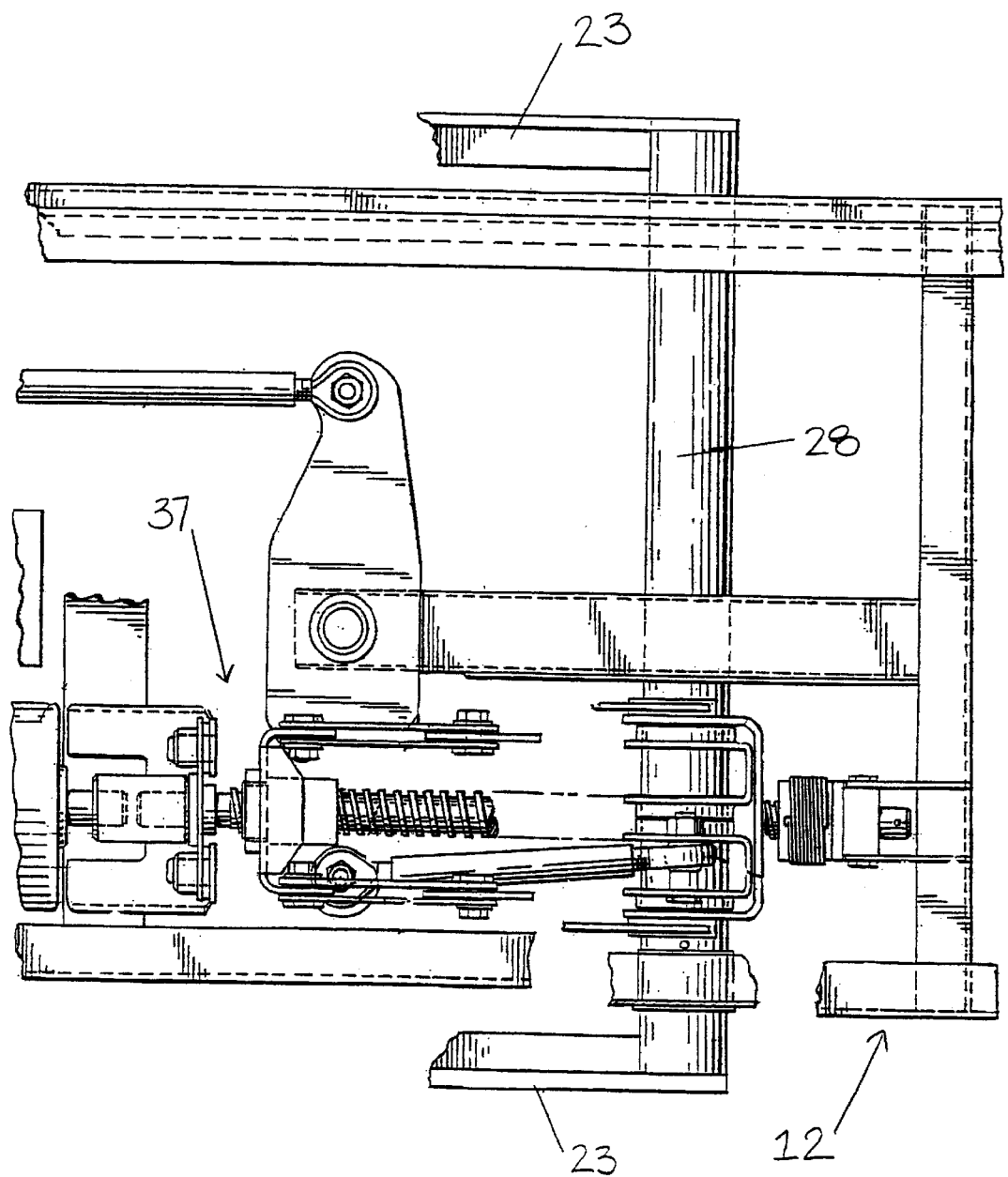
FIG. 2 is a top view of the elevational adjustment mechanism of the bed of FIG. 1.

To facilitate vertical adjustment of the bed 11, a lift mechanism 35 (FIG. 2) extends between the torque bars 27 and 28, each having thereon a traveling nut 37. When the traveling nuts 37 are moved outward, i.e. toward the head and foot ends 12 and 13 of the bed 11, by a motor driven screw (not shown), the torque bars 27 and 28 are pushed away from one another. Outward movement of the torque bars 27 and 28 causes the lift arms 22 and 23 to pivot about their respective pivot points 24 and 26. Since the torque bars 27 and 28 are rigidly attached to the respective lift arms 22 and 23, this will result in a downward movement of the torque bars 27 and 28. The frame 18 will thus be moved downward to move the bed 11 toward its lowest position. When the traveling nuts 37 are moved inward, toward the center of the bed 11, the torque bars 27 and 28 are pulled toward one another. The lift arms 22 and 23 thus pivot about their respective pivot points 24 and 26, resulting in an upward movement of the torque bars 27 and 28. The frame 18 is moved upward to elevate the bed 11 toward its highest position. The mechanism 35 is conventional and is disclosed in U.S. Pat. No. 3,958,283, which issued to Adams et al. on May 25, 1976, and is incorporated herein by reference.

The structures and operation of the components of the bed 11 thus far described are conventional. Thus, further detailed description of these components is believed unnecessary to disclose the structure and function of the present invention.

Figure 3A:
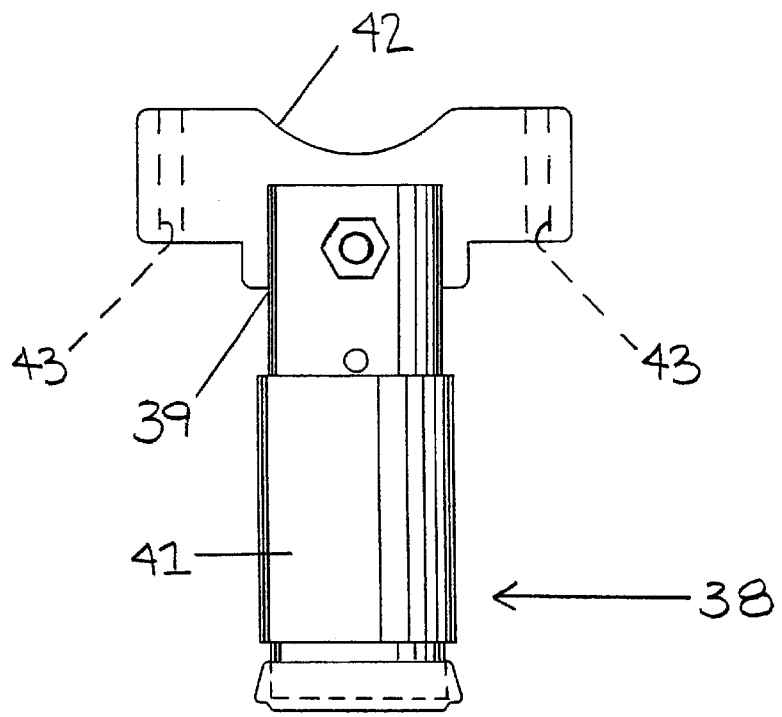
FIG. 3A is a front view of one load cell mounted on the bed of FIG. 1.

Attached to the bed 11 is the patient movement detection system 10. The detection system 10 includes a number of compressible load cells 38 (FIGS. 3A and 3B) that are coupled to the torque bars 27 and 28. When the detection system 10 is configured as illustrated herein, two load cells 38 are coupled to each torque bar 27 and 28.

Each load cell 38 includes a generally T-shaped member 39 that is received in a sleeve 41 that is sized and shaped to allow the T-shaped member 39 to slide vertically therein. The top surface of the T-shaped member 39 includes a central indention 42. The indentation 42 is shaped complementary to the cross-section of the associated torque bar 27, 28 to which the load cell 38 will be coupled. Bores 43 extend through the T-shaped member 39 on either side of the central indention 42.

To mount one of the load cells 38 on the respective torque bar 27, 28, the load cell 38 is positioned so that the central indentation 42 receives the torque bar 27, 28 as illustrated in FIG. 1. The load cell 38 is positioned directly beneath, and aligned with, one of the torque bar brackets 32, 34. A suitable fastener, such as a bolt or a screw, extends through the each of the bores 43 in the T-shaped member 39 into a bore (not shown) in the associated torque bar bracket 32, 34 to secure the load cell 38 to the bed 11.

Figure 4:
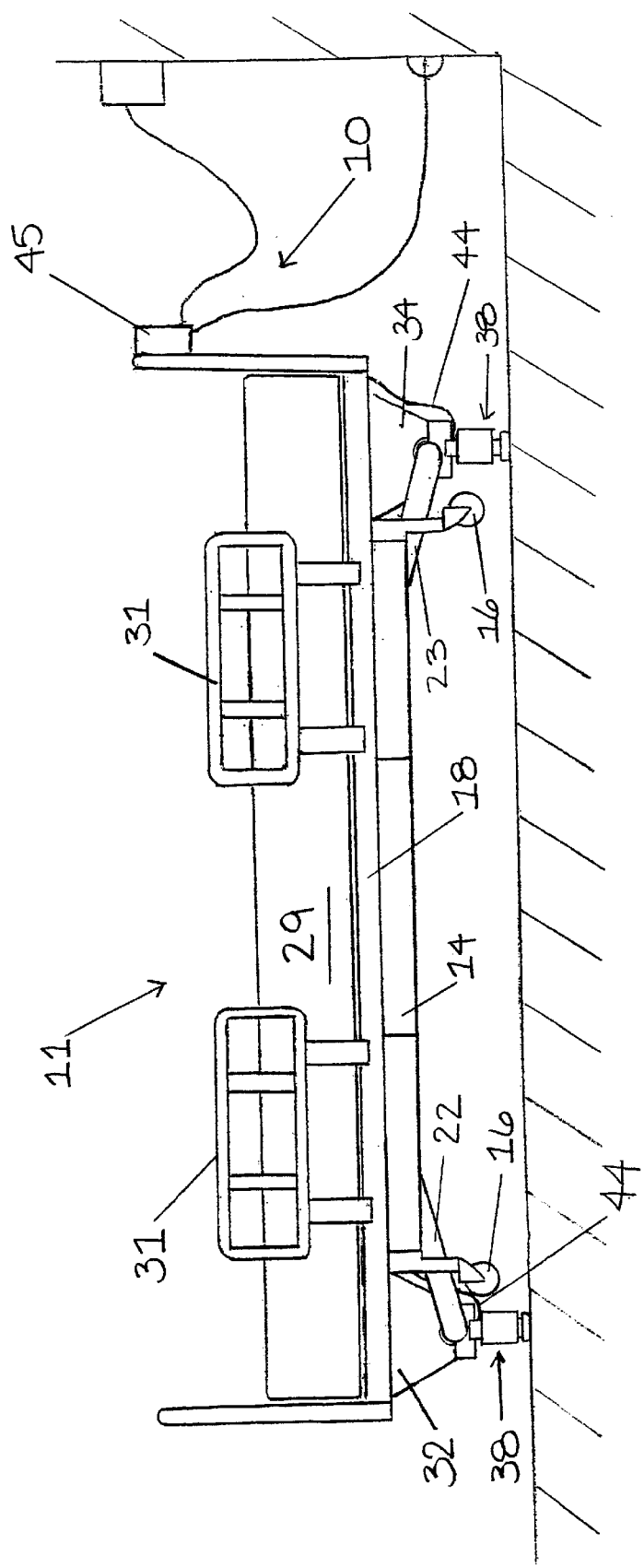
FIG. 4 is a side view of the bed of FIG. 1 in its lowest position supported only by the load cells.

As illustrated in FIG. 1, when the elevational position of the bed 11 exceeds a minimum height, the load cells 38 are out of contact with the floor. Referring now to FIG. 4, the T-shaped member 39 and the sleeve 41 of each load cell 38 are of sufficient length to allow the bed 11 to be supported only on the load cells 38 when the bed is lowered below the minimum height. To place the bed in this position, the torque bars 27 and 28 are moved outward by the traveling nuts 37. The lift arms 22 and 23 are thus pivoted about their respective pivot points 24 and 26 to lower the bed 11. Once the load cells 38 engage the floor, the torque bars 27 and 28 can no longer be moved downward toward the floor by the pivoting of the lift arms 22 and 23. Further pivoting movement of the lift arms 22 and 23 will therefore result in the base unit 14, and thus the feet of the bed or the provided wheels 16, being raised. Thus, further outward movement of the traveling nut 37 will lift the feet or the wheels 16 from the floor. In this lower position, the bed 11 is supported only by the four intermediately spaced load cells 38.

Figure 3B:
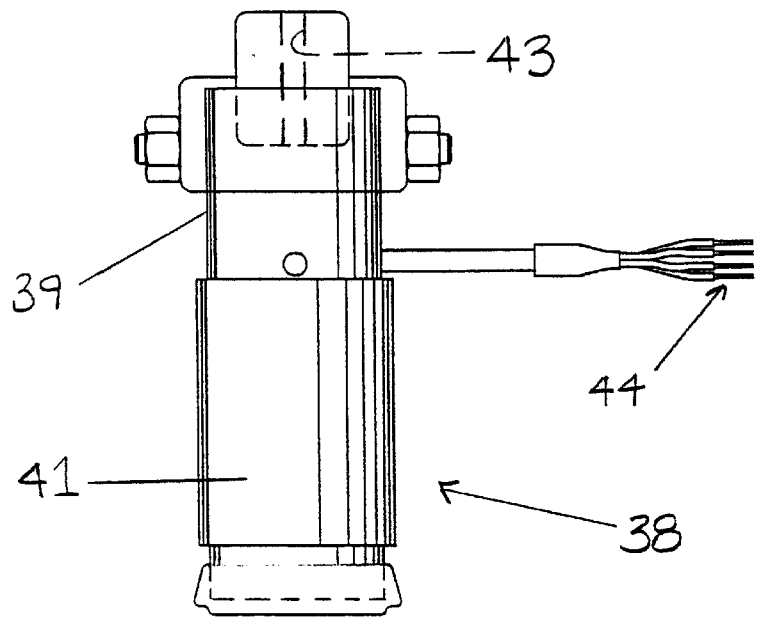
FIG. 3B is a side view of one load cell mounted on the bed of FIG. 1.

Extending from each of the load cells 38 are one or more wires 44 (FIG. 3B). The wires 44 electrically connect the load cells 38 to a control unit 45 (FIG. 4) that is attached to, or positioned near, the bed 11. Load readings, such as from a not illustrated conventional piezoelectric device oriented between the T-shaped member 39 and sleeve 41 of the load cells 38, caused by relative movement between the sleeve 41 and T-shaped member 39, are transmitted to the control unit 45. The control unit 45 includes a microprocessor (not shown) that utilizes the load readings to determine patient information. For instance, the load readings can be used by the control unit 45 to determine the weight or a patient positioned on the bed 11. Likewise, a center of gravity for the patient can also be calculated by the control unit 45. A method of determining the center of gravity from load cell output is disclosed in U.S. Pat. No. 5,276,432, which issued to Travis on Jan. 4, 1994 and is incorporated herein by reference. The control unit 45 is configured to send a signal to an appropriate location, such as a nurses' station, when the center of gravity position that it detects is positioned in an undesirable location.

OPERATION

When the load cells 38 are not engaged with the floor, the patient movement detection system 10 is inactive. When it is desired to activate the patient movement detection system 10 to monitor the movement of a patient, the bed 11 is adjusted to its lowest position by outward movement of the traveling nuts 37. As the bed 11 is lowered, the load cells 38 engage the floor, thus preventing the lift arms 22 and 23 from further pivoting toward the floor. Further outward movement of the traveling nuts 37 causes the base unit 14 to raise, thereby lifting the wheels 16 from the floor. The bed 11 is now supported only by the four intermediately spaced load cells 38.

Once the bed 11 is supported only by the load cells 38, a variety of patient information can be determined. For instance, once activated, each load cell 38 will transmit a load signal to the control unit 45. The control unit 45 can determine the weight of a patient supported on the mattress 29 from these load signals. The patient weight data can be stored by the control unit 45 or transmitted to an appropriate location, such as a patient information database. Thus, when it is desired to obtain a weight measurement for the patient, the detection system 10 can be activated and the control unit 45 can calculate the weight and transmit it to a desired location, without the need to move the patient from the bed.

The control unit 45 can also utilize the load signals transmitted from the load cells 38 to determine the location of the center of gravity of the patient. For example, when the patient shifts his or her weight in the bed 11, or attempts to move from the bed 11, the load detected by each of the load cells 38, and output to the control unit 45, will change. The control unit 45 uses the altered load data from the load cells 38 to determine a new location of the patient's center of gravity relative to the bed 11. The location of the center of gravity will be evaluated to determine its proximity to a preprogrammed acceptable zone on the mattress 29. If the patient's center of gravity is no longer located within the acceptable zone, the control unit 45 transmits an alarm to the nearby nurses' station, or otherwise alerts an appropriate caregiver that the patient is attempting to get out of bed 11. The nurse, or other caregiver, can then check on the patient to prevent him or her from leaving the bed 11 unaided and possibly suffering an injury.

When utilized to determine the center of gravity location for a patient, the patient movement detection system 10 can detect patient movement with respect to any number of zones of any desired size. One possible application of this invention, disclosed herein for illustrative purposes only, allows the patient movement detection system 10 to detect movement of the patient with respect to three preprogrammed zones.

Figure 5:
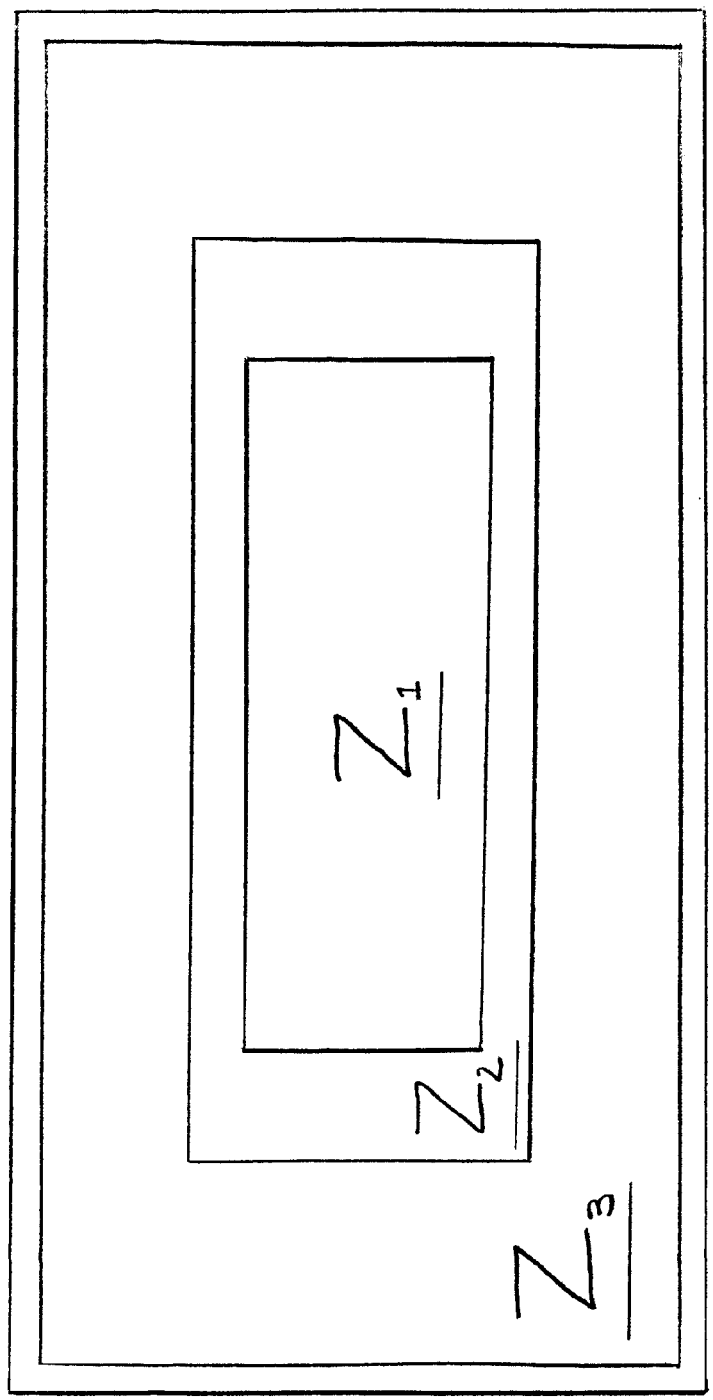
FIG. 5 is a top schematic view of the bed of FIG. 1 illustrating one possible use of the patient movement detection system of the present invention.

For example, when the detection system 10 is activated, it could be set to operate in one of three modes, corresponding to detection of patient movement with respect to three preprogrammed zones, illustrated in FIG. 5. The detection system 10 could be set to operate in the first mode when virtually no movement of the patient is desired. As illustrated in FIG. 5, the first zone $Z_1$ is relatively small, so that slight movement of the patient will cause the detection system 10 to send an alert. Operation in this mode might be desirable when a number of tubes and/or sensors are hooked up to the patient that should not be disturbed, such as immediately following surgery.

In this example, the detection system 10 could be set to have a second, intermediate operating mode corresponding to zone $Z_2$ in FIG. 5. As illustrated, the second zone $Z_2$ is larger than the first zone $Z_1$, but is still smaller than the perimeter of the mattress. This operating mode could be used when restricted movement of the patient is allowed but extended change of position is not desired. When the detection system 10 is operating in this mode, the patient could briefly move or readjust an arm or leg without setting off the alarm. However, extended change of position resulting in a center of gravity located beyond the second zone $Z_2$ will cause the control unit 45 to transmit an alarm signal.

Finally, the detection system 10 in this example could have a third operating mode that allows patient movement within a third, larger zone $Z_3$. As illustrated in FIG. 5, the third zone $Z_3$ is only slightly smaller than the perimeter of the mattress 29. Operation in this mode might be desirable when the patient is allowed unrestricted movement in bed 11, but should not leave the bed 11 without assistance. Thus, the alarm would be triggered only when the center of gravity of the patient moves beyond one of the edges of the bed 11, such as when the patient starts to stand beside the bed 11.

The patient movement detection system of the present invention can be easily retrofitted to an existing hospital bed. The cost of this patient movement detection system is considerably less than the cost of a single bed including an incorporated movement detection system. Since the patient movement detection system of the present invention is designed to be retrofitted to an existing bed, hospitals and other health care facilities can benefit from load cell based patient movement systems without purchasing a multitude of new beds.

It should be appreciated that the foregoing description is for the purposes of illustration only, and further alternative embodiments of this invention are possible without departing from the scope of the claims. For instance, while a hospital bed having four load cells has been illustrated, the present invention could be carried out with only two load cells attached to one end of the bed frame. Thus, a hospital bed having one end, typically the head end, mounted to the wall could be utilized with the present invention. In this instance, two load cells could be attached to the foot end of the bed, such that when the load cells engage the floor, the wheels, or other supports, at this end of the bed are raised from the floor.

Thus, although particular preferred embodiments of the present invention have been disclosed in detail for illustrative purposes, it will be recognized that variations or modifications lie within the scope of the present invention and do not depart from the spirit of the invention, as set forth in the foregoing description and drawings, and in the following claims.

What is claimed is:

1. In a bed having a base unit, two pairs of lift arms pivotally attached to said base unit, a torque bar extending between each pair of lift arms, a frame secured to the torque bars and a traveling nut mechanism connected to each of the torque bars and configured to move the bed between upper and lower elevational positions, the improvement comprising a plurality of load cells attached to said frame, each said load cell including an indentation sized to receive said respective torque bar, said plurality of load cells being electrically connected to a control unit that is configured to receive signals from said plurality of load cells and to determine patient information, said plurality of load cells being configured so that the bed is supported only by said plurality of load cells when the bed is in the lower position.

2. The apparatus of claim 1, wherein each load cell includes a T-shaped member slidably received in a sleeve.

3. The apparatus of claim 1, wherein said patient information includes a center of gravity for a patient on the bed.

4. The apparatus of claim 3, wherein said bed is divided into plural zones and said patient information includes which of the zones corresponds to the center of gravity of a patient.

5. The apparatus of claim 1, wherein said load cells are positioned at first and second ends of said frame and each of the load cells at the first end of said frame are secured to a different element of said frame than each of the load cells at the second end of said frame.

6. The apparatus of claim 1, wherein said torque bar is oriented transverse to the length of said bed.

7. In a bed having a base unit, two pairs of lift arms pivotally attached to said base unit, a torque bar extending between each pair of lift arms, torque bar brackets securing each of the torque bars to a frame, and a traveling nut mechanism connected to each of the torque bars and configured to move the bed between upper and lower elevational positions, the improvement comprising a plurality of load cells attached to said frame, said plurality of load cells being electrically connected to a control unit that is configured to receive signals from said plurality of load cells and to determine patient information, said plurality of load cells being configured so that the bed is supported only by said plurality of load cells when the bed is in the lower position; wherein each load cell is aligned with and attached to a respective torque bar bracket.

8. The apparatus of claim 2, wherein said patient information is determined based on relative movement between each said T-shaped member and each said respective sleeve.

9. The apparatus of claim 7, wherein said torque bar is oriented transverse to the length of said bed.

10. In a bed having a base unit, two pairs of lift arms pivotally attached to said base unit, a torque bar extending between each pair of lift arms, a frame secured to the torque bars and a traveling nut mechanism connected to each of the torque bars and configured to move the bed between upper and lower elevational positions, the improvement comprising a plurality of load cells retrofittingly attached to said frame, each said load cell includes an indentation sized to receive said respective torque bar, said plurality of load cells being electrically connected to a control unit that is configured to receive signals from said plurality of load cells and to determine patient information, said plurality of load cells being configured so that the bed is supported only by said plurality of load cells when the bed is in the lower position.

11. The apparatus of claim 10, wherein each load cell includes a T-shaped member slidably received in a sleeve.

12. The apparatus of claim 11, wherein said patient information is determined based on relative movement between each said T-shaped member and each said respective sleeve.

13. The apparatus of claim 10, wherein said patient information includes a center of gravity for a patient on the bed.

14. The apparatus of claim 13, wherein said bed is divided into plural zones and said patient information includes which of the zones corresponds to the center of gravity of a patient.

15. In a bed having a base unit, two pairs of lift arms pivotally attached to said base unit, a torque bar extending between each pair of lift arms, torque bar brackets securing each of the torque bars to a frame, and a traveling nut mechanism connected to each of the torque bars and configured to move the bed between upper and lower elevational positions, the improvement comprising a plurality of load cells retrofittingly attached to said frame, said plurality of load cells being electrically connected to a control unit that is configured to receive signals from said plurality of load cells and to determine patient information, said plurality of load cells being configured so that the bed is supported only by said plurality of load cells when the bed is in the lower position;

wherein each load cell is aligned with and attached to a respective torque bar bracket.

* * * * *